United States Patent
Lück

(10) Patent No.: US 9,597,296 B2
(45) Date of Patent: Mar. 21, 2017

(54) SUPPLEMENTATION OF PROPANE-1,2,3-TRIOL AND WATER IN FASTING SUBJECTS

(76) Inventor: Stephan Lück, Köln (DE)

(*) Notice: Subject to any disclaimer, the term of this patent is extended or adjusted under 35 U.S.C. 154(b) by 1209 days.

(21) Appl. No.: 12/999,343

(22) PCT Filed: Jan. 16, 2009

(86) PCT No.: PCT/EP2009/050512
§ 371 (c)(1),
(2), (4) Date: Jan. 19, 2011

(87) PCT Pub. No.: WO2010/006817
PCT Pub. Date: Jan. 21, 2010

(65) Prior Publication Data
US 2011/0112014 A1    May 12, 2011

(30) Foreign Application Priority Data
Jul. 16, 2008  (EP) .................... 08160550

(51) Int. Cl.
| | | |
|---|---|---|
| A61K 38/00 | (2006.01) | |
| A61P 3/02 | (2006.01) | |
| A61K 31/047 | (2006.01) | |
| A61K 31/205 | (2006.01) | |
| A61K 31/375 | (2006.01) | |
| A61K 31/47 | (2006.01) | |
| A61K 31/51 | (2006.01) | |
| A61K 31/714 | (2006.01) | |
| A61K 33/00 | (2006.01) | |
| A61K 33/06 | (2006.01) | |
| A61K 33/14 | (2006.01) | |
| A61K 33/42 | (2006.01) | |
| A61K 45/06 | (2006.01) | |
| A61K 47/10 | (2006.01) | |

(52) U.S. Cl.
CPC .......... *A61K 31/047* (2013.01); *A23L 33/15* (2016.08); *A23L 33/16* (2016.08); *A23L 33/175* (2016.08); *A61K 31/205* (2013.01); *A61K 31/375* (2013.01); *A61K 31/47* (2013.01); *A61K 31/51* (2013.01); *A61K 31/714* (2013.01); *A61K 33/00* (2013.01); *A61K 33/06* (2013.01); *A61K 33/14* (2013.01); *A61K 33/42* (2013.01); *A61K 45/06* (2013.01); *A61K 47/10* (2013.01)

(58) Field of Classification Search
CPC .......... A61K 2300/00; A61K 31/205; A61K 31/375; A61K 31/47; A61K 31/51; A61K 31/714; A61K 33/00; A61K 33/06; A61K 33/14; A61K 33/42; A61K 31/047; A61K 45/06; A61K 47/10; A23L 1/302; A23L 1/304
See application file for complete search history.

(56) References Cited

U.S. PATENT DOCUMENTS

| | | | | |
|---|---|---|---|---|
| 4,981,687 | A * | 1/1991 | Fregly et al. | 424/439 |
| 5,089,477 | A * | 2/1992 | Fregly et al. | 514/23 |
| 5,147,650 | A * | 9/1992 | Fregly et al. | 424/439 |
| 5,236,712 | A * | 8/1993 | Fregly et al. | 424/439 |
| 5,238,684 | A * | 8/1993 | Fregly et al. | 424/439 |
| 6,489,331 | B1 * | 12/2002 | Shimada et al. | 514/220 |
| 7,683,027 | B2 * | 3/2010 | Green | A61K 38/26 424/1.69 |
| 7,767,239 | B1 * | 8/2010 | Dullien et al. | 426/72 |
| 2002/0110621 | A1 * | 8/2002 | Robergs et al. | 426/74 |
| 2002/0197352 | A1 * | 12/2002 | Portman | 426/72 |

FOREIGN PATENT DOCUMENTS

| | | |
|---|---|---|
| CA | 2 223 033 A1 | 9/1999 |
| WO | 94 25031 A | 11/1994 |
| WO | 2006 008552 A | 1/2006 |

OTHER PUBLICATIONS

Maughan et al. Influence of a 36 h fast followed by refeeding with glucose, glycerol or placebo on metabolism and performance during prolonged exercise in man. Eur J Appl Physiol, 1988, vol. 57, pp. 570-576.*
Merriam Webster, An Encyclopaedia Britannica Company, definition of fast accessed at http://www.merriam-webster.com/dictionary/fast on Nov. 19, 2014, 2 pages.*
Baker et al. A new hypoglycemic syndrome: Fasting and reactive hypoglycemia, normal growth and deficient plasma growth hormone (HGH). Pediatric Research 1971, vol. 5, pp. 396-397.*
Panic attacks and glycerine. 2007. accessed online at http://www.uncommonforum.com/viewtopic.php?t=24713 on Jul. 21, 2015. 4 pages.*
Symptoms of hypoglycemia (and the adrenaline response). 2008 Accessed online at http://www.holistic-doc-pain-support.com/hypoglycemia.html on Jul. 21, 2015 . 4 pages.*
Burt et al. Hypoglycemia with glycerol infusion as antineoplastic therapy: a hypothesis. Surgery 1985, vol. 97, No. 2, pp. 231-233.*
Brisson D et al. (2001) Glycerol: a neglected variable in metabolic processes? BioEssays 23: 534-542.
Cahill G F Jr (1998) Survival in starvation. J Clin Nutr 68: 1-2.
Jahoor F et al. (1990) The relationship between gluconeogenic substrate supply and glucose production in humans. Am J Physiol 258: E288-E296.
Owen 0 E et al. (1998) Protein, fat, and carbohydrate requirements during starvation: anaplerosos and cataplerosis. Am J Clin Nutr 68: 12-34.
Patsouris D et al. (2004) PPARα governs glycerol metabolism. J Clin Invest 114: 94-103.

(Continued)

*Primary Examiner* — Marcela M Cordero Garcia
(74) *Attorney, Agent, or Firm* — Norris McLaughlin & Marcus, P.A.

(57) ABSTRACT

This invention relates to use of glycerol-containing solutions for improving both the metabolic and hydration state of fasting individuals. The same solutions can be utilized in persons facing situations where urination is impossible or inconvenient.

6 Claims, 3 Drawing Sheets

(56) References Cited

OTHER PUBLICATIONS

Figure 1:
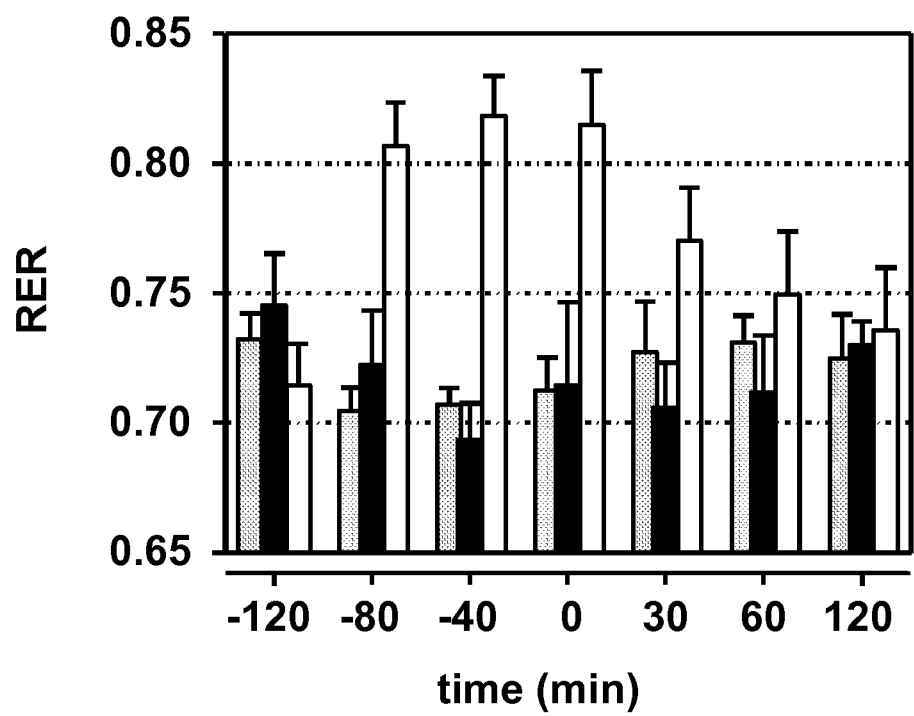

Sommer S et al. (1993) Pharmakokinetics of glycerol administered orally in healthy volunteers. Arzneim-Forsch/Drug Res 43: 744-747,.

Tao R C et al. (1983) Glycerol: its metabolism and use as an intravenous energy source. JPEN 7: 479.488.

Trimmer J K (2001) Autoregulation of glucose production in men with a glycerol load during rest and exercise. Am J Physiol 280:E657-E668.

Bier, et al., "Report of the IDECG Working Group on lower and upper limits of carbohydrate and fat intake"; European Journal of Clinical Nutrition (1999) 53, Suppl 1, pp. S177.

Klein et al., "Carbohydrate restriction regulates the adaptive response to fasting"; The American Physiological Society, 1992, pp. E631-E636.

Westman et al., "Low-carbohydrate nutrition and metabolism 1-3"; The American Journal of Clinical Nutrition, 2007, 86, pp. 276-284.

Baba et al., "Glycerol Gluconeogenesis in Fasting Humans"; Nutrition vol. 11, No. 2,1995 149-153.

Bergman et al., "Glycerol metabolism and gluconeogenesis in the normal and hypoglycemic ketotic sheep"; American Journal of Physiology, vol. 215, No. 4, Oct. 1968.

Miller et al., "Effect of glycerol feeding on endurance and metabolism during prolonged exercise in man"; Medicine and Science in Sports and Exercise vol. 15, No. 3, 1983.

Plowman et al; "Exercise Physiology for Health, Fitness, and Performance" Second Edition, Copyright 2008 Lippincott Williams & Wilkins, Chapter 5.

Terblanche et al., "Effects of glycerol feeding before and after exhausting exercise in rats"; J. Appl. Physiol.: Respirat. Environ. Exercise Physiol. 50 (1): 94-101, 1981.

Wagner; "Hyperhydrating with glycerol: Implications for athletic performance"; Journal of the American Dietetic Association, 1999; 99: 207-212.

European patent No. 2300008 opposition papers and cited references filed May 12, 2016.

\* cited by examiner

SUPPLEMENTATION OF PROPANE-1,2,3-TRIOL AND WATER IN FASTING SUBJECTS

This application is a 371 of PCT/EP2009/050512, filed Jan. 16, 2009, which claims priority of EP 08160550.3, filed Jul. 16, 2008, incorporated herein by reference.

The present invention provides preparations supporting glycerol-based gluconeogenesis in fasting subjects. The invention further provides glycerol-containing preparations preventing dehydration during fasting. The same preparation may also be utilized in humans facing situations where urination is impossible or inconvenient.

BACKGROUND OF THE INVENTION

During fasting, the natural metabolite glycerol (propane-1,2,3-triol), a component of triacylglycerols, is liberated in the process of lipolysis. Through the final steps of the gluconeogenetic pathway it is easily converted to glucose, mainly in the liver. It has been shown that the regulation of hepatic glycerol metabolism plays a pivotal role in fasting [Patsouris, D. et al., J. Clin. Invest. 114: 4-103 (2004)].

Assuming a total energy expenditure of 10.000 kJ per day, about 250 g of body fat will have to be oxidized to meet the energy demand. This is equivalent to about 1 mol of typical free fatty acids such as palmitic acid or stearic acid. In the context of lipolysis, this means a liberation of, at best, ⅓ mol of glycerol, i.e. about 30 g, which may be converted to 30 g glucose. The daily glucose demand of the adult human brain and of other strictly glucose-dependent tissues is in the order of 100 g-160 g. As a consequence of this physiological glycerol deficit in fasting humans, other glucose precursors, in particular amino acids, become substrates of gluconeogenesis, resulting in undesirable protein losses, in particular during the early stages of fasting [Owen, O. E. et al., Am. J. Clin. Nutr. 68:12-34 (1998)]. Animals, with smaller brain mass in relation to their body weight than humans, generally show a more favourable balance of glucose demand and glycerol liberation during fasting. Some species thus manage to survive long periods of starvation without protein losses [Bernard, S. F. et al., J. Exp. Biol. 205:2745-2754 (2002)]. It has been shown in mammals that infusion of glycerol inhibits gluconeogenesis from other precursors [Steele, R. et al., Am. J. Physiol. 221:883-888 (1971)]. This generally suggests that gluconeogenetic protein losses in fasting humans may be reduced by glycerol supplementation. In contrast to ingestion of glucose and other carbohydrates, glycerol supplementation does not increase plasma glucose concentrations in healthy fasting subjects. Moreover, glycerol application does not increase hepatic glucose production beyond fasting control conditions without exogenous glycerol load [Trimmer, J. K. et al., Am. J. Physiol. 280:E657-E668 (2001)]. This means that glycerol supplementation will not affect the metabolic state of fasting: fatty acid oxidation remains the major source of energy supply. Since adequate glycerol supplementation during fasting improves glucose availability, it reduces undesirable effects such as hypoglycaemia, gluconeogenetic protein losses and increased levels of ketone bodies.

In addition to endogenous glucose production, hydration is a critical topic during fasting. Reducing food intake also reduces water intake. Fasting subjects practically never adapt their drinking habits spontaneously and sufficiently to compensate for these losses. Nutritional consultants therefore prescribe strict schemes of fluid intake for fasting subjects. Simply drinking increased amounts of pure water rarely meets with success, because it decreases the osmolarity of body fluids, which in turn leads to rapid water excretion via the Adiuretin pathway. Application of iso- or hyperosmotic glycerol solutions during short- and long-term fasting will not only provide a substrate for gluconeogenesis but also induce a longer-lasting hydration. As stated supra, glycerol is a natural metabolite and non-toxic in large doses—European food laws permit application quantum satis. When consumed, it is rapidly absorbed from the gastrointestinal tract. Distribution space of glycerol depends on plasma concentrations: In the range of low plasma concentrations (<5 mmol/l) it approximates 0.3 l per kg body weight. With larger concentrations, distribution space increases to about 0.6 l/kg, i.e. near to total body water volume [Beylot, M. et al., J. Lipid. Res. 28:414-422 (1987); Robergs, R. A. et al., Sports Med. 26:145-167 (1998)]. Below plasma concentrations of 1 mmol/l, glycerol is fully reabsorbed by the kidneys. Above this limit, both tubular reabsorption and renal excretion increase over a large range of concentrations.

Besides serving as substrate for gluconeogenesis, glycerol can be oxidized in many tissues or be used for re-esterification of fatty acids [van Hall, G. et al., J. Physiol. 543: 1047-1058 (2002)]. This, however, occurs only at a slow rate, so that the disappearance rate of glycerol is much slower than that of, for example, glucose. Given the slow disappearance rate and the large distribution volume, isoosmotic or hyperosmotic glycerol solutions will lead to long-lasting hydration effects.

Persons facing situations where urination is impossible or inconvenient (e.g. long distance car driving, various occupational contexts), tend to abstain from fluid consumption in order to reduce the need to urinate. Elderly people, who per se display reduced fluid intake, frequently undergo deliberate dehydration in the late afternoon and evening hours in order to avoid frequent urination overnight. The situation gets worse if neither fluid nor food is consumed, because hypoglycaemia may add to dehydration. Both hypoglycaemia and dehydration reduce mental and physical fitness, which may be hazardous in some situations. In the elderly, for example, it will increase the risk of falling. In this field of application, subjects may also benefit from the hydrating and anti-hypoglycaemic effect of the present glycerol solutions.

WO 94/25031 discloses an exercise regimen which enhances exercise endurance and performance. The regimen includes pre-exercise hydration with a glycerol solution combined with hydration during exercise with a glycerol-based solution to prolong hydration effects. The first pre-exercise glycerol solution regimen begins 2 h prior to exercise and ends ½ h before exercise begins. The hydration during exercise regimen combines glycerol with carbohydrate and sodium to additionally compensate for glycogen depletion and the sweat losses of sodium during exercise. Further WO 06/008552 and CA-A-2233033 disclose aqueous (re)hydrating compositions comprising glycerol.

The problem underlying present invention is the insufficient endogenous glycerol supply and the dehydration seen in deliberately fasting subjects as well as in subjects trying to avoid urination. The present invention presents glycerol as suitable agent that helps preventing hypoglycaemia, dehydration and gluconeogenetic protein losses in such contexts.

SHORT DESCRIPTION OF THE INVENTION

It was found that solutions providing adequate amounts and concentrations of glycerol can be used to stabilize blood glucose concentrations in fasting subjects, thus reducing the reliance on ketone bodies and the gluconeogenetic transformation of amino acids into glucose. In addition, the same preparation counteracts dehydration in fasting subjects as well as in subjects undergoing dehydration in order to avoid urination.

More preferably, said preparations are liquid compositions, and even more preferably, said liquid compositions are beverages containing glycerol. In a further preferred embodiment, the glycerol concentration in the composition is from 0.2 to 1 mol/l. In a further embodiment, preparation comprises additional compounds improving palatability and/or further nutritional supplements such as electrolytes, vitamins, vitamin-related additives, proteins, amino acids, dyes, flavouring agents, stabilizing agents, and functional additives. Thus, the present invention provides:

(1) the use of a liquid containing glycerol for preparing a liquid preparation for supporting fasting subjects and for reduction of the need to urinate;
(2) a preferred embodiment of aspect (1), wherein the liquid preparation is a beverage containing glycerol in the range of 0.2 to 1.0 mol/l preferably 0.4 to 0.8 mol/l;
(3) a liquid composition containing glycerol for supporting fasting subjects, and for reduction of the need to urinate;
(4) embodiment of aspect (3), wherein the preparation is a beverage containing glycerol in the range of 0.2 to 1.0 mol/l preferably 0.4 to 0.8 mol/l;
(5) a method for fasting which comprises administering the fasting subject a liquid composition comprising glycerol as defined in aspect (3) or (4) above; and
(6) a method for reducing the need to urinate in a subject which comprising administering the subject a liquid composition comprising glycerol as defined in aspect (3) or (4) above.

SHORT DESCRIPTION OF THE FIGURES

FIG. 1: Respiratory exchange ratio (RER, means±SE) in 8 fasting male subjects after administration of isoosmotic glycerol solution (290 mmol/l, hatched bars), hyperosmotic glycerol solution (580 mmol/l, filled bars), and carbohydrate solution (60 g/l, white bars). 2 l of each beverage were consumed between −120 and −40 min.

Figure 2:
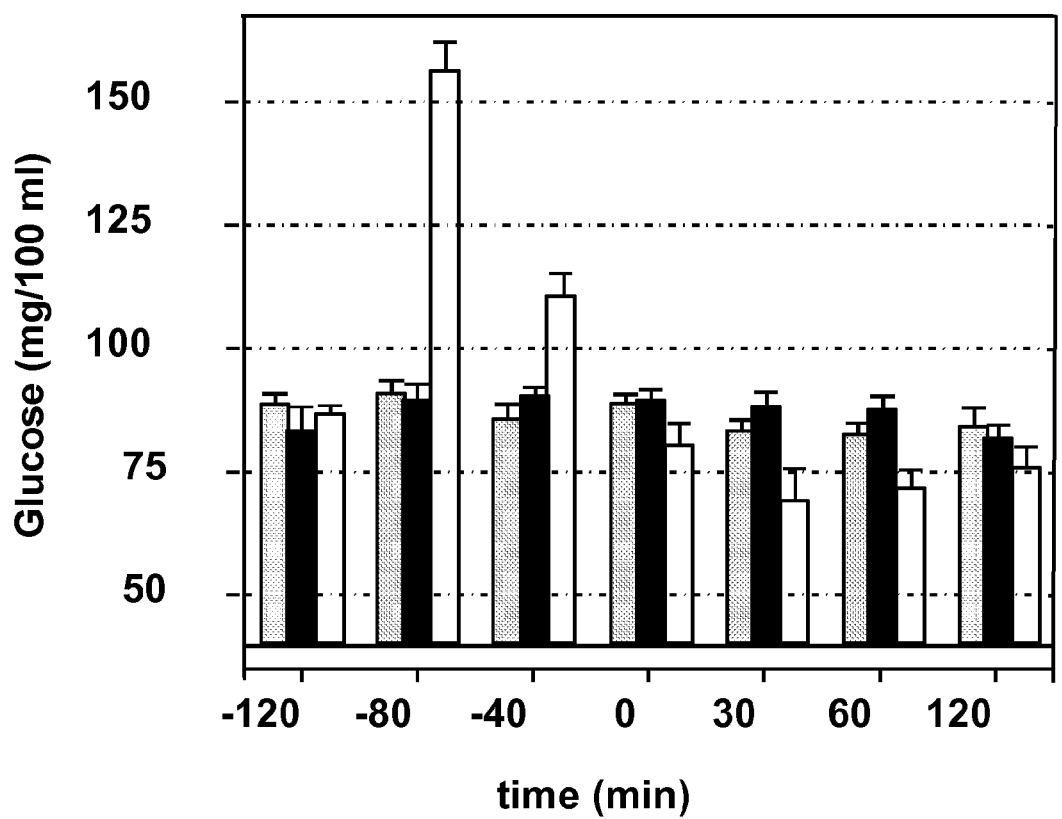

FIG. 2: Blood glucose concentrations (means±SE) in 8 fasting male subjects after administration of isoosmotic glycerol solution (290 mmol/l, hatched bars), hyperosmotic glycerol solution (580 mmol/l, filled bars), and carbohydrate solution (60 g/l, white bars). 2 l of each beverage were consumed between −120 and −40 min.

Figure 3:
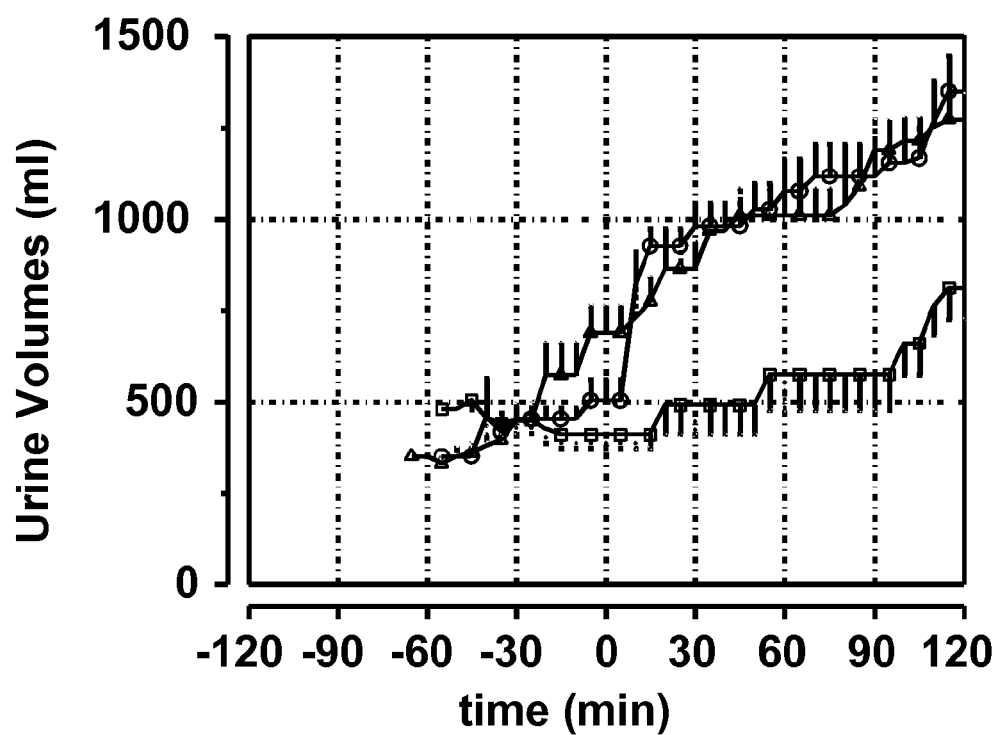

FIG. 3: Cumulated urine volumes (means±SE) in 8 fasting male subjects after administration of isoosmotic glycerol solution (290 mmol/l, triangles), hyperosmotic glycerol solution (580 mmol/l, squares), and carbohydrate solution (60 g/l). 2 l of each beverage were consumed between −120 and −40 min.

DETAILED DESCRIPTION OF THE INVENTION

The present invention describes use of glycerol in liquid preparation and liquid composition for supporting fasting subjects, and for reducing the need to urinate. The fasting includes short- and long-duration fasting. The liquid preparation/composition for reducing the need to urinate is particularly applicable for geriatric care. Thus, the liquid preparation/composition according to the invention can be applied in medical applications that are controlled by a medical practitioner. Glycerol is liberated from adipose tissue during fasting and converted into glucose through gluconeogenesis, mainly in the liver. Due to an unfavourable relationship of brain mass and overall energy demand, fasting humans liberate far less glycerol (about 30 g per day) than required to meet the glucose demands of the brain (about 120 g per day) and other glucose-dependent tissues. As a consequence amino acids and other glucose precursors become substrates of glyconeogenesis and ketone bodies have to be derived from free fatty acids to compensate for the remaining energy deficit of the brain. Glycerol supplied by the compositions of present invention improves glucose availability for the brain during fasting. Thus it reduces undesirable effects such as hypoglycaemia, gluconeogenetic protein losses and increased levels of ketone bodies. Since the capacity of endogenous glucose production is limited, glycerol does not increase blood glucose levels in healthy fasting subjects (FIG. 2). Moreover, the respiratory exchange ratio during fasting is practically unaffected by glycerol application (FIG. 1). This means that glycerol, in contrast to carbohydrates, does not increase the contribution of carbohydrates to energy supply. In other words: glycerol does not disturb the metabolic state of fasting.

In addition to hypoglycaemia, gluconeogenetic loss of amino acids, and ketosis, dehydration is a further side effect of fasting. Glycerol permeates membranes, particularly via aquaglyceroporins. At isoosmotic concentrations (290 mmol/l) and above, its distribution volume approaches the total body water space. Due to the osmotic effect of glycerol, the water of such glycerol solutions is also distributed over its maximal distribution space. As a consequence, potential counter-regulation induced by volume-receptors of fluid volume regulation—situated in the walls of the low-pressure part of the circulation—is minimal. With isoosmotic or higher concentrations of glycerol, the second group of receptors associated with fluid and electrolyte control of the body, osmoreceptors, would signal either an undisturbed osmolarity or a lack of water. The rate-limiting step of excess water removal from the body is, therefore, the slow disappearance rate of glycerol. Glycerol supplied by the compositions of present invention has the second effect of improving hydration of fasting subjects.

Long-lasting hydration of the body also means less urine production per time (FIG. 3). In this aspect, the glycerol solutions of the present invention may support subjects facing situations where urination is impossible or inconvenient, e.g. in long-distance car driving or in many occupational contexts. In a preferred embodiment, this invention is specifically valuable to older people who tend to consume too little water in the evenings so not to be forced to get up at night in order to urinate. This frequent behaviour deteriorates the effect of already diminished thirst sensation among the elderly. Therefore, in one aspect, this invention is specifically targeted at improving living conditions of the elderly, but also to psychologically help persons forced to undergo situation where urination is impossible. Since such situations are frequently associated with short-term fasting, e.g. an overnight fast in the elderly, the aforementioned hypoglycaemia-preventing capability of glycerol may add to its hydration effect, thus further improving mental and physical fitness.

Depending on total energy expenditure, and thus endogenous glycerol liberation, as well as brain mass, a fasting adult will require a glycerol supplementation in the order of 100 g±40 g per day (4.2 g±1.7 g per hour) to obtain the optimal metabolic effect of glycerol. On the other hand, appreciable hydration effects of glycerol are only seen with concentrations above 0.2 mol/l (18 g/l). Therefore, solutions of the present invention contain at least 0.2 mol/l, preferably 0.3 to 1 mol/l, more preferably 0.4 to 0.8 mol/l.

Of note, solutions containing too high concentrations of glycerol can potentially lead to stomach upsets, vomiting and diarrhoea in healthy subjects. Similarly, fast consumption of large doses may lead to cerebral dehydration resulting in headaches, dizziness and blurred vision.

Similarly, application of glycerol may cause hypervolemia and is contraindicated in subjects with reduced heart function or hepatic or renal diseases or when reduction of urine flow is not desired.

Therefore, in another aspect of present invention, compositions do not contain more than 1 mol/l of glycerol.

Additionally, in a further aspect, the composition contains additives such as electrolytes, vitamins, vitamin-related additives, amino acids, proteins, dyes, flavouring agents, and stabilizing agents.

Added electrolytes are chosen from the group of sodium, potassium, calcium, chloride, phosphorous, and magnesium. Too high concentrations of electrolytes could have negative effects on electrolyte resorption and general physical performance, wherefore the concentration range is chosen so that positive and no negative effects are obtained. Therefore, in a further aspect of the present invention, the concentration of electrolytes in the composition is:
- 10-400 mg/l sodium, preferably about 300 mg/l; and/or
- 10-300 mg/l potassium, preferably about 200 mg/l; and/or
- 10-200 mg/l chloride, preferably about 150 mg/l; and/or
- 10-200 mg/l phosphorous, preferably about 150 mg/l; and/or
- 5-200 mg/l magnesium, preferably about 100 mg/l; and/or
- 5-200 mg/l calcium, preferably about 100 mg/l.

In a further aspect, vitamins and/or vitamin-related additives are added to the solution. In a preferred embodiment, the vitamins and/or vitamin-related additives added are chosen from vitamin B1, vitamin B11, vitamin B12, vitamin C, and L-carnitine. More preferably, the preferred concentrations of the vitamins and vitamin-related additives added depend upon an undersupply or specific demand and are:
- 1-100 mg/l ascorbic acid (vitamin C), preferably about 30 mg/l; and/or
- 0.50-5 mg/l thiamine (vitamin B1), preferably about 1.0 mg/l; and/or
- 100-600 µg/l folic acid/folat/pteroylglutamate (vitamin B11), preferably about 400 µg/l; and/or
- 1-10 µg/l cobalamine (vitamin B12), preferably about 5 µg; and/or
- 100-4000 mg L-carnitine, preferably about 1000 mg.

In a further aspect, flavouring agents and dyes are added to confer an appealing appearance to the composition. Suitable flavouring agents and dyes are chosen from all authorized additives, especially natural flavouring agents and dyes (phenolic compounds and isoprenoidic compounds like phenolics, carotenoids, flavonoids, terpenes etc.)

In a further aspect, stabilizing agents are contained in the composition. In a more preferred embodiment, stabilizing agents are chosen from the group of benzoic acid, propionic acid, and antioxidants.

In a further embodiment, the present invention comprises an instant composition, from which the liquid composition of the present invention can be generated by dissolution in water. This instant composition can be on hand as a powder or as syrupy liquid or paste.

The following examples will further expatiate on the benefits of present invention.

These examples however are not to be construed as limiting the invention.

EXAMPLES

Example 1

Determination of the Respiratory Exchange Rate Upon Administration of Carbohydrate, Isoosmotic, and Hyperosmotic Glycerol Solution The respiratory exchange ratio (RER) upon administration of carbohydrate (60 g/l), isoosmotic (290 mmol/l), and hyperosmotic (580 mmol/l) glycerol solution was studied in 8 male subjects aged between 22 and 35 years. After an overnight fast, each subject consumed 2 l of one solution (between −120 min and −40 min in FIG. 1). All subjects had to ingest all types of solution, however in random order. Oxygen consumption and $CO_2$ output for RER determination were measured over 5 min periods at the times given in FIG. 1. Simultaneously, blood samples were taken and analyzed for plasma glucose and haemoglobin concentration as well as haematocrit. RER measurements confirmed that all subjects were in a fasting state. In contrast to the carbohydrate solution, RER remained in the fasting range after administration of the glycerol beverages. As expected, blood glucose concentration remained unaffected by glycerol application but increased after carbohydrate ingestion (FIG. 2). In conjunction with the RER results (FIG. 1), this shows that consumption of glycerol has no appreciable effect on energy metabolism during fasting.

Example 2

Determination of the Cumulated Urine Volumes Upon Administration of Carbohydrate, Isoosmotic, and Hyperosmotic Glycerol Solution The cumulated urine volumes upon administration of carbohydrate (60 g/l), isoosmotic (290 mmol/l), and hyperosmotic (580 mmol/l) glycerol solution was studied in 8 male subjects aged between 22 and 35 years. After an overnight fast and emptying their urinary bladder, each subject consumed 2 l of one solution (between −120 min and −40 min in FIG. 3). All subjects had to ingest all types of solution, however in random order. Urine was collected over a period of 3 hours (between −60 min and 120 min in FIG. 3). While the isoosmotic glycerol solution induced only a short delay of urine output in comparison with the carbohydrate beverage, the hyperosmotic glycerol concentration lead to a substantial reduction of urine production over the measurement period.

The invention claimed is:

1. A method for reducing hypoglycaemia in a fasting subject without affecting the respiratory exchange ratio of fasting, wherein in said fasting subject fatty acid oxidation is the major source of energy supply, said method comprising administering to said fasting subject a liquid composition comprising glycerol in an amount of 0.2 to 1.0 mol/l and reducing hypoglycaemia in said fasting subject without affecting the respiratory exchange ratio of fasting.

2. The method of claim 1, wherein the liquid composition further comprises one or more compounds that improve the palatability of the liquid composition and/or one or more nutritional supplements selected from the group consisting of electrolytes, vitamins, vitamin-related additives, proteins, amino acids, dyes, flavouring agents and stabilizing agents.

3. The method of claim 2, wherein the liquid composition comprises one or more electrolytes selected from the group consisting of sodium, potassium, magnesium, calcium, chloride, and phosphorous.

4. The method of claim 2, wherein the liquid composition comprises mineral nutrients in a content of mineral nutrients per liter of liquid composition of:
   10-400 mg sodium; and/or
   10-300 mg potassium; and/or
   10-200 mg chloride; and/or
   10-200 mg phosphorous; and/or
   5-200 mg magnesium; and/or
   5-200 mg calcium.

5. The method of claim 2, wherein the liquid composition comprises: (a) one or more vitamins and vitamin-related additives selected from the group consisting of vitamin B1, vitamin B11, vitamin B12, vitamin C, and L-carnitine and wherein the content of vitamins and vitamin-related additives per liter is 1-100 mg vitamin C; and/or 0.50-5 mg vitamin B1; and/or 100-600 μg vitamin B11; and/or 1-10 μg vitamin B12; and/or 100-4000 mg L-carnitine; and/or
   (b) one or more flavouring agents selected from the group consisting of natural flavouring agents and dyes; and/or
   (c) one or more stabilizing agents selected from the group consisting of benzoic acid, propionic acid, and antioxidants.

6. The method of claim 1, wherein the liquid composition is prepared from a liquid or solid concentrate.

\* \* \* \* \*